(12) United States Patent
Lee et al.

(10) Patent No.: US 7,951,448 B2
(45) Date of Patent: *May 31, 2011

(54) MATERIAL FOR CREATING MULTI-LAYERED FILMS AND METHODS FOR MAKING THE SAME

(75) Inventors: Amy Lee, Mountain View, CA (US); Michael A. Evans, Palo Alto, CA (US)

(73) Assignee: Nellix, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/858,274

(22) Filed: Aug. 17, 2010

(65) Prior Publication Data

US 2010/0312267 A1 Dec. 9, 2010

Related U.S. Application Data

(63) Continuation of application No. 11/752,750, filed on May 23, 2007, now Pat. No. 7,790,273.

(60) Provisional application No. 60/802,951, filed on May 24, 2006.

(51) Int. Cl.
*A61F 2/06* (2006.01)
*B32B 3/10* (2006.01)
*B32B 27/06* (2006.01)
*B32B 27/16* (2006.01)
*B32B 27/40* (2006.01)

(52) U.S. Cl. .................. 428/306.6; 428/308.4; 428/422; 428/423.1; 623/1.2; 623/1.44

(58) Field of Classification Search .................. None
See application file for complete search history.

(56) References Cited

U.S. PATENT DOCUMENTS

| | | | |
|---|---|---|---|
| 4,565,738 | A | 1/1986 | Purdy |
| 4,641,653 | A | 2/1987 | Rockey |
| 4,728,328 | A | 3/1988 | Hughes et al. |
| 5,530,528 | A | 6/1996 | Houki et al. |
| 5,534,024 | A | 7/1996 | Rogers et al. |
| 5,665,117 | A | 9/1997 | Rhodes |
| 5,693,088 | A | 12/1997 | Lazarus |
| 5,769,882 | A | 6/1998 | Fogarty et al. |
| 5,800,512 | A | 9/1998 | Lentz et al. |
| 5,824,037 | A | 10/1998 | Fogarty et al. |
| 5,843,160 | A | 12/1998 | Rhodes |
| 5,867,762 | A | 2/1999 | Rafferty et al. |

(Continued)

FOREIGN PATENT DOCUMENTS

FR 2834199 A1 7/2003

(Continued)

OTHER PUBLICATIONS

Gilling-Smith, "Stent Graft Migration After Endovascular Aneurysm Repair," presented at 25th International Charing Cross Symposium, Apr. 13th, 2003 [Power Point Presentation and Transcript], 56 pages total.

(Continued)

*Primary Examiner* — Ramsey Zacharia
(74) *Attorney, Agent, or Firm* — Kilpatrick Townsend and Stockton LLP

(57) ABSTRACT

The present invention provides multilayered materials, such as films usable in particular in medical devices in the form of vascular grafts, biocompatible coverings, and/or inflatable bladders, prosthesis for the endoluminal treatment of aneurysms, particularly aortic aneurysms including both abdominal aortic aneurysms (AAA's) and thoracic aortic aneurysms (TAA's).

28 Claims, 8 Drawing Sheets

U.S. PATENT DOCUMENTS

| | | | |
|---|---|---|---|
| 5,876,448 | A | 3/1999 | Thompson et al. |
| 5,888,660 | A | 3/1999 | Landoni et al. |
| 5,928,279 | A | 7/1999 | Shannon et al. |
| 5,931,866 | A | 8/1999 | Frantzen |
| 5,994,750 | A | 11/1999 | Yagi |
| 6,022,359 | A | 2/2000 | Frantzen |
| 6,083,259 | A | 7/2000 | Frantzen |
| 6,110,198 | A | 8/2000 | Fogarty et al. |
| 6,168,592 | B1 | 1/2001 | Kupiecki et al. |
| 6,187,034 | B1 | 2/2001 | Frantzen |
| 6,190,402 | B1 | 2/2001 | Horton et al. |
| 6,193,745 | B1 | 2/2001 | Fogarty et al. |
| 6,196,230 | B1 | 3/2001 | Hall et al. |
| 6,261,305 | B1 | 7/2001 | Marotta et al. |
| 6,283,991 | B1 | 9/2001 | Cox et al. |
| 6,290,722 | B1 | 9/2001 | Wang |
| 6,296,603 | B1 | 10/2001 | Turnlund et al. |
| 6,299,597 | B1 | 10/2001 | Buscemi et al. |
| 6,312,462 | B1 | 11/2001 | McDermott et al. |
| 6,312,463 | B1 | 11/2001 | Rourke et al. |
| 6,331,184 | B1 | 12/2001 | Abrams |
| 6,334,869 | B1 | 1/2002 | Leonhardt et al. |
| 6,409,757 | B1 | 6/2002 | Trout, III et al. |
| 6,463,317 | B1 | 10/2002 | Kucharczyk et al. |
| 6,506,204 | B2 | 1/2003 | Mazzocchi |
| 6,544,276 | B1 | 4/2003 | Azizi |
| 6,592,614 | B2 | 7/2003 | Lenker et al. |
| 6,613,037 | B2 | 9/2003 | Khosravi et al. |
| 6,656,214 | B1 | 12/2003 | Fogarty et al. |
| 6,663,607 | B2 | 12/2003 | Slaikeu et al. |
| 6,663,667 | B2 | 12/2003 | Dehdashtian et al. |
| 6,695,833 | B1 | 2/2004 | Frantzen |
| 6,730,119 | B1 | 5/2004 | Smalling |
| 6,827,735 | B2 | 12/2004 | Greenberg |
| 6,843,803 | B2 | 1/2005 | Ryan et al. |
| 6,918,926 | B2 | 7/2005 | Letort |
| 6,960,227 | B2 | 11/2005 | Jones et al. |
| 7,530,988 | B2 | 5/2009 | Evans et al. |
| 7,666,220 | B2 | 2/2010 | Evans et al. |
| 7,790,273 | B2 | 9/2010 | Lee et al. |
| 2001/0044655 | A1 | 11/2001 | Patnaik et al. |
| 2002/0026217 | A1 | 2/2002 | Baker et al. |
| 2002/0045848 | A1 | 4/2002 | Jaafar et al. |
| 2002/0045931 | A1 | 4/2002 | Sogard et al. |
| 2002/0052643 | A1 | 5/2002 | Wholey et al. |
| 2003/0014075 | A1 | 1/2003 | Rosenbluth et al. |
| 2003/0051735 | A1 | 3/2003 | Pavcnik et al. |
| 2003/0130725 | A1 | 7/2003 | DePalma et al. |
| 2003/0135269 | A1 | 7/2003 | Swanstrom |
| 2003/0204242 | A1 | 10/2003 | Zarins et al. |
| 2003/0204249 | A1 | 10/2003 | Letort |
| 2003/0216802 | A1 | 11/2003 | Chobotov et al. |
| 2004/0016997 | A1 | 1/2004 | Ushio |
| 2004/0044358 | A1 | 3/2004 | Khosravi et al. |
| 2004/0082989 | A1 | 4/2004 | Cook et al. |
| 2004/0098096 | A1 | 5/2004 | Eton |
| 2004/0116997 | A1 | 6/2004 | Taylor et al. |
| 2004/0167607 | A1 | 8/2004 | Frantzen |
| 2004/0204755 | A1 | 10/2004 | Robin |
| 2005/0004660 | A1 | 1/2005 | Rosenbluth et al. |
| 2005/0028484 | A1 | 2/2005 | Littlewood |
| 2005/0065592 | A1 | 3/2005 | Holzer |
| 2006/0212112 | A1 | 9/2006 | Evans et al. |
| 2007/0150041 | A1 | 6/2007 | Evans et al. |
| 2008/0039923 | A1 | 2/2008 | Taylor et al. |
| 2009/0198267 | A1 | 8/2009 | Evans et al. |
| 2009/0318949 | A1 | 12/2009 | Ganpath et al. |
| 2009/0319029 | A1 | 12/2009 | Evans et al. |
| 2010/0004728 | A1 | 1/2010 | Rao et al. |
| 2010/0036360 | A1 | 2/2010 | Herbowy et al. |

FOREIGN PATENT DOCUMENTS

| | | |
|---|---|---|
| WO | WO 00/51522 | 9/2000 |
| WO | WO 01/21108 A1 | 3/2001 |
| WO | WO 01/66038 | 9/2001 |
| WO | WO 02/102282 | 12/2002 |

OTHER PUBLICATIONS

Carmi et al., "Endovascular stent-graft adapted to the endoluminal environment: prototype of a new endoluminal approach," J Endovasc Ther. Jun. 2002;9(3):380-381.

U.S. Appl. No. 60/855,889, filed Oct. 31, 2006; first named inventor: Steven L. Herbowy.

MATERIAL FOR CREATING MULTI-LAYERED FILMS AND METHODS FOR MAKING THE SAME

CROSS-REFERENCES TO RELATED APPLICATIONS

The present application is a continuation of U.S. patent application Ser. No. 11/752,750 filed May 23, 2007, which claims the benefit of U.S. Provisional Patent Application No. 60/802,951 filed May 24, 2006, the full disclosures of which are incorporated herein by reference.

BACKGROUND OF THE INVENTION

The present invention relates generally to materials and apparatus for use in the treatment of patients. More particularly, the present invention relates to biocompatible material having greater functionality, and methods for making and using the same.

Plastic materials have long been used in medical applications, including implants. An example of such use is in treating aneurysms. Aneurysms are enlargements or "bulges" in blood vessels which are often prone to rupture and which therefore present a serious risk to the patient. Aneurysms may occur in any blood vessel, but are of particular concern when they occur in the cerebral vasculature or the patient's aorta. The present invention is particularly concerned with biocompatible materials, including multilayer materials, for use in such applications.

A material for use in medical treatment, in particular implantable devices, requires many attributes which need to work in synergy to provide for optimum performance. Examples of such attributes include: ease of deployment (in case of use as a deployable component), adaptable configuration for design and use within various tortuous lumens of the body, ease of manufacture, and/or identification and tracking during treatment procedures.

A commonly used biocompatible material is polytetrafluoroethylene (PTFE). PTFE is chemically inert, thus desirable for use in medical devices that come in contact with the human body. However, material, such as films formed from PTFE may lack, or possess less than desirable properties such as ease of processing into desired forms.

For at least these reasons, it would desirable to provide improved biocompatible material, in particular those for use in treatment of aortic aneurysms.

BRIEF SUMMARY OF THE INVENTION

The present invention provides materials, such as films, methods for making and using the same, and systems. In particular, such material is employable in medical devices in the form of vascular grafts, biocompatible coverings, inflatable bladders, prosthesis for the endoluminal treatment of aneurysms, particularly aortic aneurysms including both abdominal aortic aneurysms (AAA's) and thoracic aortic aneurysms (TAA's). In an exemplary embodiment, the materials of the present invention are usable in forming the walls of devices for use in the treatment of AAA. Examples of such suitable structures and devices are described in co-pending provisional patent application Ser. No. 60/855,889, entitled "Methods and Systems for Aneurysm Treatment," filed on Oct. 31, 2006, and assigned to the assignee of the present invention, the full disclosure of which is hereby incorporated by reference.

The present invention provides for a multi-layered structure with a first layer comprising a fluorinated material; and at least one second layer (polymer backbone) formed from a second polymeric material, and disposed adjacent a surface of the first layer.

The fluorinated material forming the first layer may be selected from any suitable fluorinated material, including but not limited to, FEP, PFA, ETFE, PTFE, ePTFE, or any combinations thereof. In an exemplary embodiment, the first layer is formed from ePTFE. For purposes of describing the invention, PTFE (polytetrafluoroethylene) and ePTFE (expanded polytetrafluoroethylene) will be used as the exemplary fluorinated material.

As used herein, it should be understood that the term "layer" is broadly used and is not restricted to a layer formed from a molecular layer. It should also be appreciated by those skilled in the art, that a multilayer material, formed from different materials, may include an interface which includes the materials of the adjacent layers. In other words, the interface between two different layers may be formed which includes a mixture of the materials from the different layers.

Depending on the intended use of the composite material, it might be desirable for the composite material to have a tensile strength in only one or multiple directions. To achieve the desired tensile strength, PTFE may be stretched (prior to sintering) in one or more directions (i.e., along one or more axes). The stretching of the PTFE will impart greater tensile strength in the direction of the stretch. In an exemplary embodiment, such direction may be in a single direction, while in other exemplary embodiments, the PTFE may be stretched along multiple axes (including bi-axial). The more the number of axes along which the PTFE is stretched, the more tensile strength it will be imparted to the PTFE in all such directions. In an exemplary embodiment, the multilayer material has a high tensile strength/low elongation along a single axis. In other exemplary embodiments, the composite material has high tensile strength/low elongation along multiple axes.

Some of the properties of native PTFE that make it attractive for use in medical devices are its high resistance to chemicals and low surface energy. However, these same properties that make PTFE attractive for use in medical applications, coupled with the extremely high temperatures required to manufacture the material, render native PTFE difficult for processing into forms/shapes/structures that may be intended for use in various applications. Another property of PTFE is its susceptibility to creep (e.g., the unwanted relative movement of PTFE molecules past one another and deformation of the parts formed from PTFE) which may be detrimental to mechanical strength and geometric stability of the structure or object which has been formed from PTFE.

To reduce some of the undesirable properties of native PTFE without losing the chemical properties that make it desirable for use in medical applications, it is processed into ePTFE, by way of stretching the PTFE (un-sintered) to induce the formation of pores or small tears. The resulting material produces a porous matrix which includes nodes and fibrils that can be modified or altered to achieve specific mechanical properties, including but not limited to, pore size, pore density, modulus of elasticity, tensile anisotropy. These various mechanical properties may be imparted based on the degree and method of expansion of the PTFE into ePTFE.

The porous nature of ePTFE is particularly attractive for long-term medical implants by providing a suitable substrate for incorporation into the host (i.e., in-growth). On the other hand, for short term or temporary implant applications in which the device will eventually be removed, in-growth is not a desirable characteristic. In either case, because the degree of in-growth has been shown to be related to the pore size of the matrix, the ePTFE can be modified to whichever mode desired.

The first and the second layers may be formed from similar or different material. By way of example, both layers may comprise fluorinated material (the same or a different fluorinated material) or the second layer may be formed from non-fluorinated material. The second layer or polymer backbone, may be formed from thermoplastic or thermoset materials. In an exemplary embodiment, the second layer is formed from a thermoplastic material.

Further processing of the composite film to create the desired structure or forms is further affected by the interaction of the secondary polymer to itself and/or to ePTFE. The secondary polymer material(s) serve as the polymer backbone and enables the processing of the subsequent steps, while the ePTFE serves as the biocompatible interface with its biological surroundings. The mechanical properties of each of the material also contribute to the overall mechanical properties of the composite film.

Suitable exemplary material forming the second layer includes any one or more of polyolefins including: low density polyethylene; polyesters including polyester terapthalate; polyurethanes formulations including biodurable aromatic polyethers including Biospan® (an aromatic polyetherurethaneurea with a soft segment of polytetramethyleneoxide (PTMO) and a hard segment of diphenylmethane diisocyanate and mixed diamines, available from companies such as the Polymer Technology Group, Berkeley Calif.) and Elasthane™ (a polyether urethane is a thermoplastic elastomer formed as the reaction product of a polyol, an aromatic diisocyanate, and a low molecular weight glycol used as a chain extender. Polytetramethylene oxide (PTMO) is reacted in the bulk with aromatic isocyanate, 4,4'-methylene bisphenyl diisocyanate (MDI), and chain extended with 1,4-butanediol, available from companies such as the Polymer Technology Group, Berkeley Calif.); polycarbonates including Bionate® (a polycarbonate urethane, available from companies such as the Polymer Technology Group, Berkeley Calif.), Chronoflex® (a medical-grade segmented polyurethane elastomers, available from companies such as CardioTech International, Wilmington, Mass.), and Carbothane® (a thermoplastic polyurethanes manufactured using the aliphatic compound, hydrogenated methylene diisocyanate (HMDI), and formulated with a polycarbonate diol (PCDO)); silicone modified polyurethanes including PurSil™ (a silicone polyether urethane available from companies such as the Polymer Technology Group, Berkeley Calif.); silicones; fluoropolymers including FEP, PFA and ETFE; and acetates including ethylene vinyl acetates; and any combinations thereof. The material forming the second layer preferably is selected such that it can seal to other materials (e.g., the first layer) at temperatures ranging from about 100° C. to about 400° C.

The polymer backbone material of the second layer may generally form about 1 to about 99 percent (%) of the total thickness of the composite material, normally from about 10 to about 90 percent.

The first and the second layers may be formed contiguously adjacent each other. Alternatively, the layers, although adjacent, may not be completely contiguous. In an embodiment, a portion of the second material impregnates a portion of the first layer. In other words, during formation of the composite film, some of the polymer backbone material will impregnate the ePTFE layer due to the porous nature of the ePTFE. Such impregnation may range from about 0.1 to about 95%, from about 5 to about 95%, normally from about 5 to about 70%.

In an exemplary embodiment, the first and second layers have compatible elongation properties which allow the film/structure to elongate without separation of the layers. In an exemplary embodiment, the elongation properties are such that the composite film does not elongate more than about 120%.

As stated earlier, the composite film may be formed such that it has high tensile strength/low elongation along a single axis or multiple axis by way of its manufacture and as described above. In an exemplary embodiment, the composite film has a high tensile strength/low elongation along a single axis.

In some exemplary embodiments, the first layer may be processed to increase its surface energy. The activation of the surface may be achieved through suitable means such as plasma treatment, laser roughening, wet chemical treatment, biological treatment, and any combinations thereof. In an embodiment, the activated surface of the first layer is the layer which is not adjacent the polymer backbone. In some instances, the biologically activated surface of the fluorinated first layer, (e.g., ePTFE) promote thrombogenesis and/or healing of an area within a patient's body which is going under treatment using structures made from the composite material.

The first and the second layer may be disposed adjacent one another by suitable means such as lamination, including thermal lamination, or film casting. The polymer backbone material, as for example, when made from elastomeric materials, may have a tendency to adhere to itself when folded over. To minimize this effect an additive may be added to the surface of the polymer backbone which is not adjacent the first layer. Examples of such additives include, but are not limited to, alumina, tantalum, or combinations thereof.

In some embodiments, the composite film may be configured for diagnostic visibility such that it, or structures made from the composite film, are echo-lucent, radio-lucent, ultrasound-lucent, CT-lucent, fluoro-lucent, or any combination thereof. To impart diagnostic visibility, the second layer may be the layer chosen to have such diagnostic visibility characteristics. Similarly, at least a portion of the composite material, preferably that of the second layer, may include markers to enhance identification of the location of the composite film, or structures which are made from the composite material, when it is disposed within a patient.

Similarly, in some embodiments, to aid in any of the delivery, placement, visualization, or fixation of the composite film, or structures made from the material, it includes structural element/s. The structural element may be disposed at any suitable location within or on the composite film. In an embodiment, the structure element is a marker for diagnostic visualization. Such markers may be made from suitable material such as, but not limited to platinum, iridium, or gold.

In some embodiments, to impart further rigidity and support to the composite film, supporting elements are incorporated into the film. The supporting element may be metallic (e.g., shape memory materials, stainless steel, cobalt chromium alloys, and any combinations thereof) or polymeric, and may be incorporated into either or both of the layers of the composite film, preferably the first layer. By way of example, the supporting material may be a stent or a polymeric mesh material.

Exemplary embodiments of multilayered material of the present invention may be formed into any shape or structure suitable for its intended purpose. By way of example, the shape of the multilayer material may be adapted to conform to an aneurysm being treated. In some instances, the multilayer material can be shaped for the aneurismal geometry of a particular patient using imaging and computer-aided design and fabrication techniques. In other instances, a family or collection of multilayer material formed into the desirable shape or structure may be developed having different geometries and sizes so that a treating physician may select a specific filling structure to treat a particular patient based on the size and geometry of that patient's aneurysm. It should be appreciated that the multilayered material described in the present invention may be used for a variety of purposes, and formed, as needed into any desirable shape or form, and that it is not limited to the treatment of an aneurysm.

For purposes of description, multilayer materials embodying the features of the present invention will be referred to as "film," "composite material," "composite film," or the like, unless otherwise indicated.

DETAILED DESCRIPTION OF THE INVENTION

The composite film may be formed by many methods, some of which will be further described below. It should be appreciated by those skilled in the art, that various features of the films of the present invention are not limited to the specific embodiment shown, and may be used and formed with other features described in relation with other exemplary embodiments.

The composite films, embodying features of the present invention, may include one or more of the following properties and may be engineered by selecting one or more of the following factors. The composite film, in some exemplary embodiments, has constrained elongation (expansibility) along one or more axes. In an exemplary embodiment, the composite film has constrained elongation (expansibility) along a single axis. Expansion of the composite film 10 may be constrained by either or both the material of the first layer (e.g., ePTFE) and the polymer backbone. As used herein, the terms elongation or expansibility refer to the ability of the composite film to stretch in one or more directions before it is torn. As stated above, for purposes of description PTFE/ePTFE will be used when describing the fluorinated material of the first layer.

The methods for creating an ePTFE composite film will vary depending on the density and porosity of the ePTFE, as well as the properties of the secondary material(s) (i.e., polymer backbone) chosen. The polymer backbone may be selected for any number of chemical and mechanical properties including biocompatibility/biostability, melt temperature, fluid permeability, chemical adhesion, elasticity/plasticity, and tensile strength. The details of the various methods will be separately discussed following the description of the various exemplary composite films and structures made therefrom.

Figure 1A:
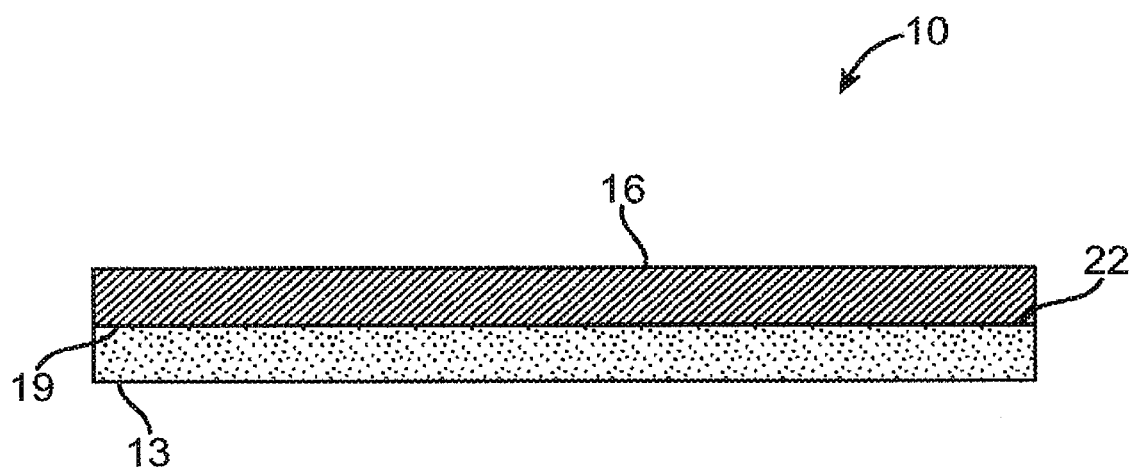
FIG. 1A is a schematic illustration of an exemplary composite film.
Figure 1B:
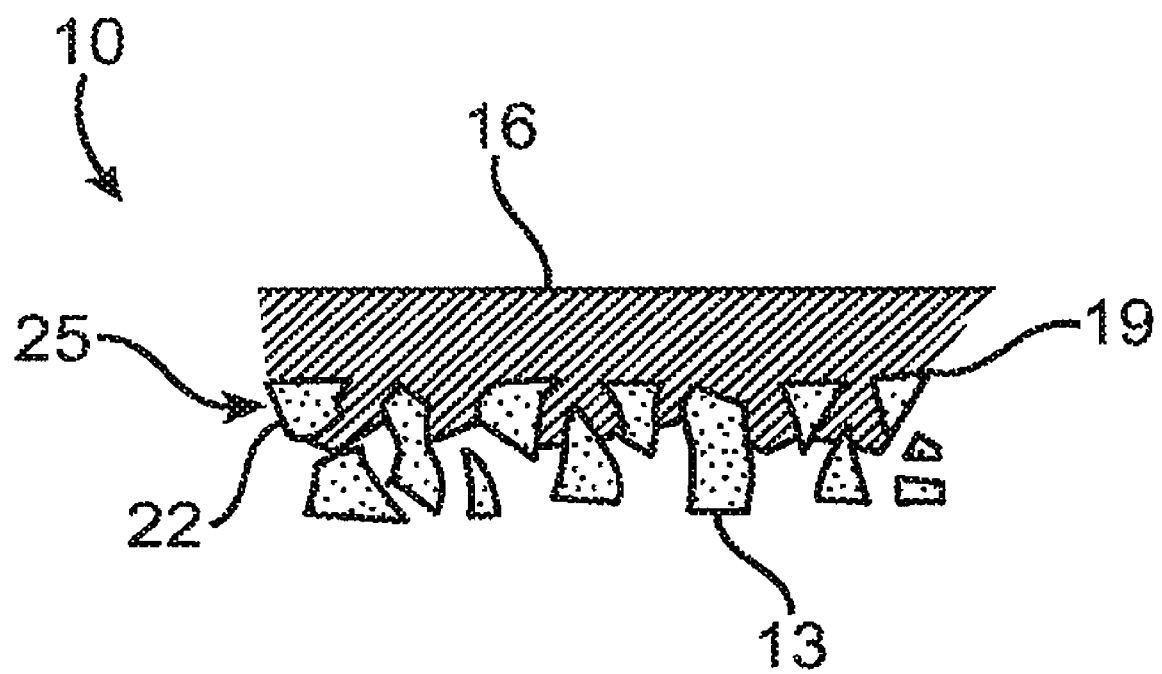
FIG. 1B is a schematic illustration of an exemplary composite film with the polymer backboone layer impregnating the porous ePTFE.

Now referring to FIGS. 1A and 1B, an exemplary composite film 10 embodying features of the present invention is illustrated. The composite film 10 includes two layers 13 and 16 formed from ePTFE and a polymer backbone, respectively. Each layer has two surfaces or sides. In the embodiment shown, a first surface 19 of the ePTFE and a first surface 22 of the polymer backbone are disposed adjacent one another. In the embodiment shown, and as can be best seen in the cross section shown in FIG. 1B, surfaces 19 and 22, of the ePTFE and the polymer backbone form an interface 25, where at least some of the pores of the ePTFE have been impregnated with the polymer backbone.

The polymer backbone may be formed from thermoset or thermoplastic material. For purposes of description, thermoplastic material will be used as the material forming the polymer backbone. In the exemplary embodiment shown in FIGS. 1A and 1B, the secondary material is a thermoplastic polymer (e.g., polyethylene, polyethylene terephthalate, FEP) which can be laminated onto ePTFE by using a combination of heat and pressure. Heating the thermoplastic to its melt temperature and applying pressure allows the thermoplastic melt to flow into the pores of the ePTFE material resulting in a mechanical bond between the two materials. Due to the chemical similarities between fluoropolymers such as FEP and ePTFE, a thermal lamination between the two materials creates an additional chemical bond besides the mechanical interlocking.

Thermoplastic materials can be applied to the ePTFE for thermal lamination in the form of sheet, or through application of powder dispersions that can be applied to the surface of the ePTFE. After application of heat and pressure, the powder will melt and reflow into a solid, contiguous layer.

The composite film 10 may also be formed by means of film casting. Suitable materials (e.g., silicones, and polyurethanes) may be placed into solution and made into very thin sheets of material by film casting onto the ePTFE which will act as the carrier material. Solutions or dispersions of such materials can also be sprayed on or directly applied to the ePTFE material in order to create the composite film. The polymer in solution flows into the pores of the ePTFE through wicking, pressure, or a combination of both, to create a mechanical interlock between the two materials similar to the configuration shown in FIG. 1B.

The polymer backbone may form a continuous composite film with the two materials (i.e., ePTFE and the polymer backbone) adhering to one another in a continuous manner. However, composite films can also be created where the materials are not fully adhered to each other. By way of example, portions of the surface 19 of the ePTFE may not be laminated or covered by the polymer backbone (not shown).

The present invention provides for several methods for creating seals/bonds between the surfaces of the different composite films to further form suitable structures.

Figure 2A:
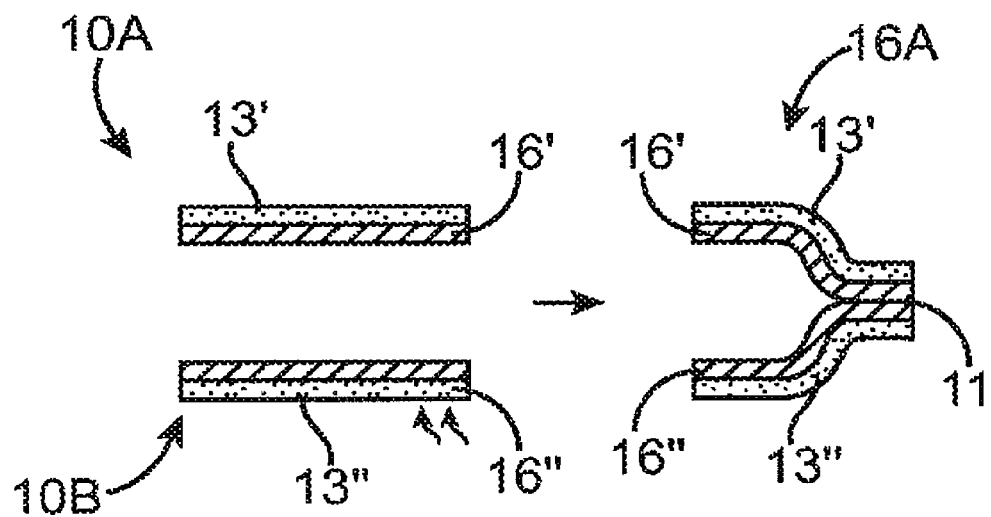
FIG. 2A is a schematic illustration of an exemplary embodiment of two composite films forming a seal between the polymer backbone layers of two composite films.
Figure 2B:
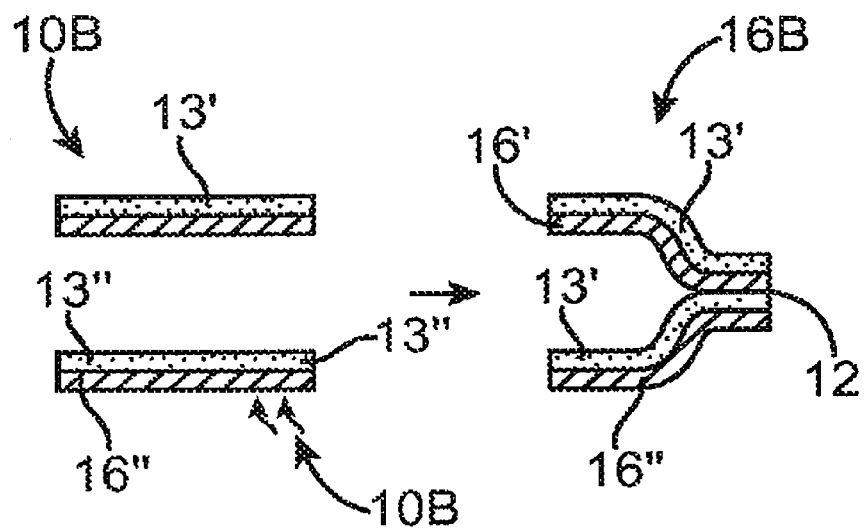
FIG. 2B is a schematic illustration of an exemplary embodiment of two composite films forming a seal between ePTFE layer of one composite film and the polymer backbone layer of another composite film.

In one exemplary embodiment as shown in FIGS. 2A through 2B, a composite film (e.g., films formed through thermal lamination) such as composite film 10 may be sealed to another composite film (made from similar or different polymer backbone material) using traditional heat sealing methods (e.g., bar/impulse heater, ultrasonic welding, hot knife, RF welding). Non-traditional methods such as laser welding may also be used, depending on the transmission properties of the polymer backbone and other additives (e.g. absorptive dyes, carbon) that can be incorporated into either the material or the sealing region.

As seen in FIG. 2A, wherein like references refer to like elements, two composite films 10A and 10B, each having an ePTFE layer (13' and 13') and a polymer backbone layer 16 (16' and 16") are positioned and set apart across from one another such that the polymer backbone layers, 16' and 16" of each composite film faces toward each other. The two composite films 10A and 10B are thermally sealed at their respective ends which are disposed across one another, forming seal 11 and a partial structure 16A. FIG. 2B illustrates another exemplary embodiment of the two composite films 10A and 10B, wherein the polymer backbone layer 16' of composite film 10A faces the ePTFE layer 13" of composite film 10B. Similarly, the two composite films 10A and 10B are thermally sealed at their respective ends which are disposed across one another, forming seal 12 and a partial structure 16B. In another exemplary embodiment, bonds can also be formed by placing a pre-cut shape of thermoplastic material sandwiched between two sheets of ePTFE material and heat treating the seam afterwards to melt the thermoplastic into the ePTFE material.

Figure 3:
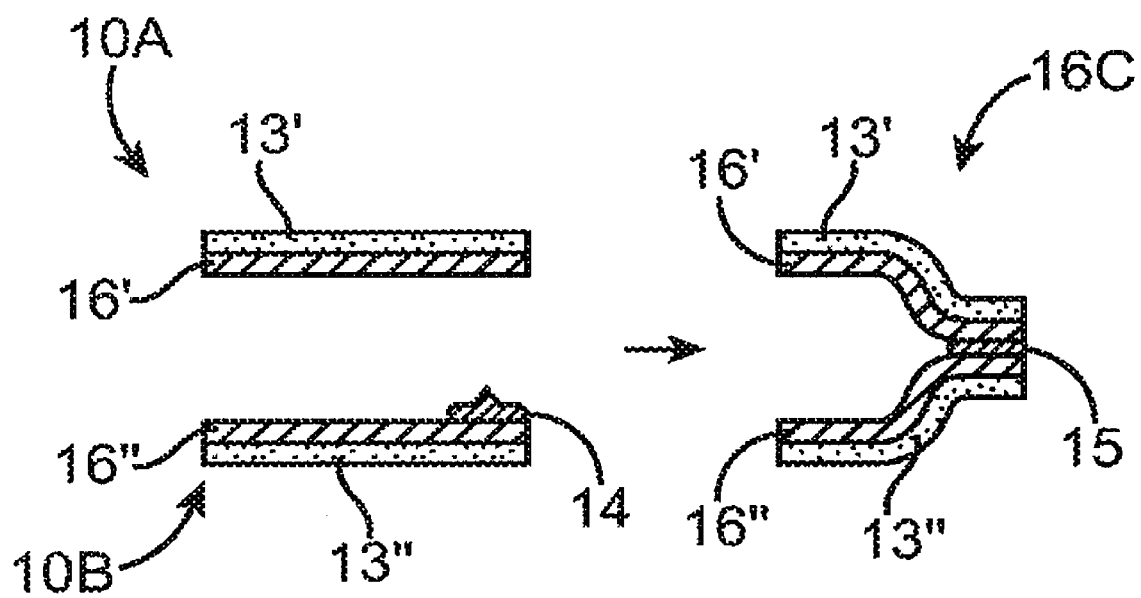
FIG. 3 is a schematic illustration of an exemplary embodiment of two composite films forming a seal between the polymer backbone layers of two composite films with an adhesive.

Now referring to FIG. 3, depending on the backbone polymer (16' and 16") selected, a chemically compatible adhesive 14 may be used to join such similar materials together (e.g., silicone adhesive to join together silicone-ePTFE composite films). The resulting bond 15 is a strong chemical bond between two sheets of the backbone polymer. FIG. 3 illustrates an exemplary embodiment of two composite films 10A and 10B similar to that shown in FIG. 2A with the adhesive 14 disposed between polymer backbone layers 16' and 16" of composite film 10B forming the bond/seal 15 at a portion of the two layers facing each other, and thus creating a partial structure 16C.

Mechanical suturing is another suitable method for creating a seam between composite films (not shown) in order to reinforce the bond between sheets of materials. The mechanical stitching may be done alone or in combination with other forms of seals/bonds, as for example those described above. In an exemplary embodiment, thermally laminated composites can be combined with mechanical suturing in a number of ways. Seams comprised of thermoplastic-thermoplastic or thermoplastic-ePTFE interfaces can be heat treated either before or after stitching to melt/reflow the thermoplastic material, strengthening the bond between sheets. In addition, sutures comprised of a thermoplastic material can melt/reflow throughout an ePTFE through a similar heat treatment process after stitching.

In yet another exemplary embodiment, when the polymer backbone of the composite film is formed from silicone, silicone adhesives can be applied at the seams and stitched while still uncured. As the silicone continues to cure, the holes in the material seal and provide the necessary bond.

The composite films 10 embodying features of the present invention may be used to create a number of structures, such as containment members including containment bags usable in medical devices and applications as those described earlier above (e.g., AAA). Some exemplary methods for forming containment members with simple and/or complex geometric shapes, including those with multiple chambered/segmented containment units; are further described below.

Figure 4C:
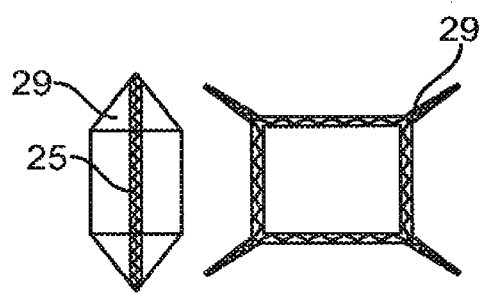
FIGS. 4A-4C are schematic illustration of an exemplary structure made using the composite films of the present invention.
Figure 4B:
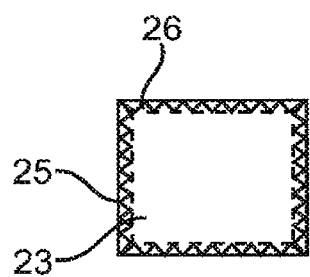
Figure 4A:
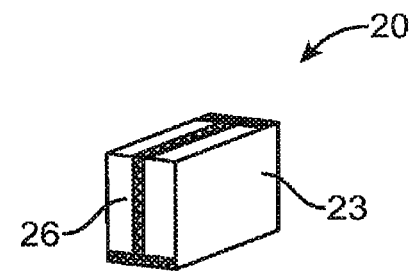

Various geometrical containment devices can be created by sealing the flat composite films 10 together to create structures with volumetric forms. One such method for creating a simple volumetric form, as shown in FIGS. 4A through 4C, is by way of incorporating gussets (i.e., triangular inserts within the seams) into the design. The volumetric member 20 shown in FIG. 4A is formed by sealing two flat sheets 23 and 26 together (FIG. 4B) in a square form with gussets 29 incorporated within the seams 25 (FIG. 4C). The sealed composite sheets are thereafter expanded to form the cube 20.

Figure 5A:
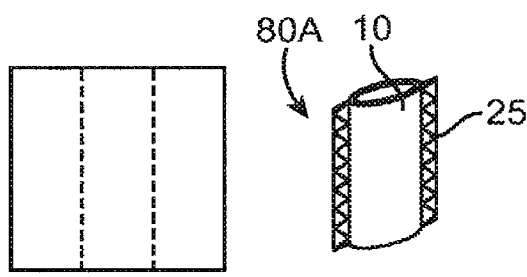
FIGS. 5A-5C are schematic illustrations of exemplary tubular structures made using the composite films of the present invention.
Figure 5C:
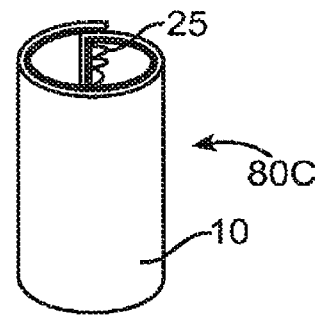
Figure 5B:
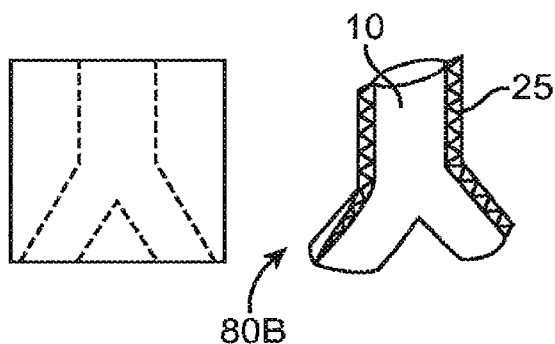

Similarly, cylindrical tubes, whether simple cylindrical tubes such as 80A, or tapered and contoured tubes such as 80B (e.g., Y-shaped as shown in FIG. 5B), as shown in FIGS. 5A and 5B, can also be formed from flat composite sheets. Another exemplary embodiment of a cylindrical tube 80C is shown in FIG. 5C, which is formed by wrapping the composite film 10 around itself and sealing it onto itself.

Figure 6:
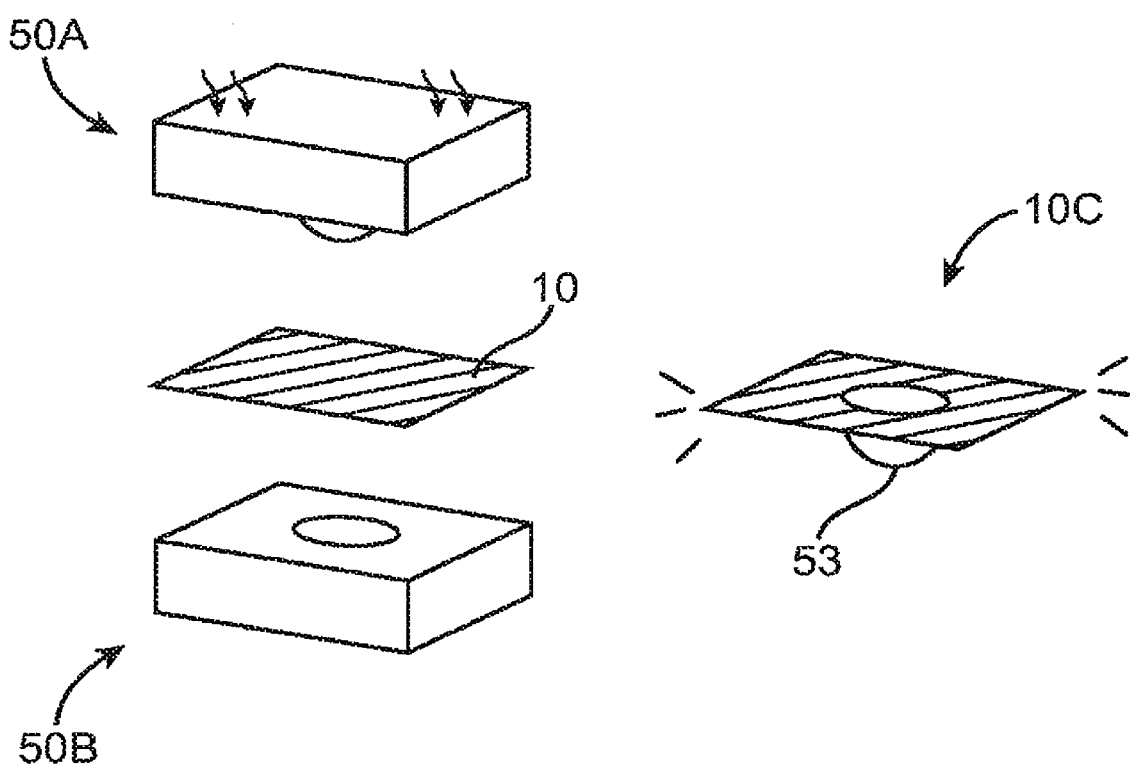
FIG. 6 is a schematic illustration of an exemplary composite film having a contoured pre-form shape.

Due to the non-porous nature of a fully covered composite films/sheet, a flat sheet of ePTFE composite can be manufactured into contoured pre-form shaped sheets through methods such as vacuum- or thermo-forming. As shown in FIG. 6, flat sheet 10 is placed between shaped molds 50A and 50B. Thereafter, heat and pressure transform the composite film into the desired shape based on the shape of the mold. Once sheet 10 has cooled, it is removed from the molds whereupon it has been transformed to a volumetric sheet 10C having an outward extending protrusion 53.

Figure 7:
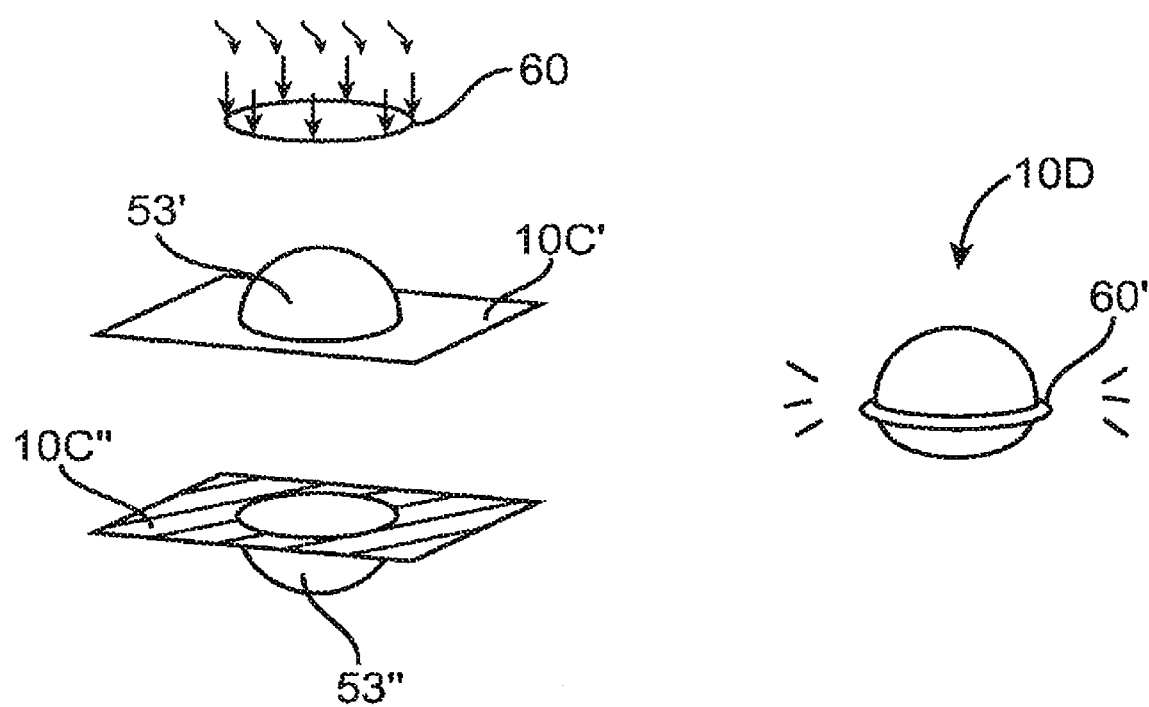
FIG. 7 is a schematic illustration of an exemplary structure formed from the composite film of FIG. 6.

FIG. 7 illustrates the use of two pre-formed volumetric sheets 10C' and 10C" as formed according to the process described in reference to FIG. 6. The two pre-formed sheets 10C' and 10C" are brought into contact with each other such that their respective protrusions 53' and 53" are on opposite surfaces of each of the sheets. Thereafter, a sealing pattern (e.g., ring 60) using a combination of heat and pressure is applied around the two sheets forming the volumetric form or containment member 10D with a ring 60'. Any additional, or unwanted parts of the composite film may be removed or excised.

The ability of the ePTFE composite films to retain the pre-form contours is a result of the combination of the plastic elongation properties of both the ePTFE and the selected polymer backbone material. In addition to the potential to make large scale pre-form shapes, the methods described herein, can similarly be used to create films with macroscopic surface texture patterns to increase the surface area of the pre-form containment members or structures, to enhance its grip or traction.

Below, additional descriptions regarding the various material and methods is provided.

Mechanical Property Modification of the Composite Film

Normally, ePTFE is stretched, at least in one direction, prior to being sintered, to induce the formation of micro-tears and thus, imparting expansibility and shapeability onto the ePTFE. The size and density of these micro-tears are what gives ePTFE its porosity and flexibility. As such, the ePTFE material typically has anisotropic tensile and elongation characteristics depending on its orientation, with the preferential yield direction being perpendicular to the initial stretch direction. Tensile properties in the stretch direction are higher and result in brittle-like fractures.

This directional stretching characteristic can be used to create forms that will yield before failure when a force is applied in the tensile direction. This expansible characteristic can be desirable for fault tolerance or used deliberately as a design feature. A composite film sealed perpendicular to the initial stretch direction results in failure before material elongation, while a composite film sealed parallel to the initial stretch direction results in material elongation before bond failure.

For example, in the case of a tube formed with composite films of the present invention, with longitudinal seams subjected to internal radial forces, the highest tensile load will be exerted circumferentially on the device using the formed tube. Thus, by orienting the seams parallel to the preferential ePTFE stretch direction, the composite can elongate under such a load before breaking.

Similarly, a stent-graft can be made from a tube of the composite material (comprised of an ePTFE that has been manufactured to allow for expansion in the radial direction and a polymer backbone with high elongation properties) by attaching it to a balloon expandable stent in its unexpanded configuration. Since the composite material has the ability to expand to great diameters without breaking, the material can expand without failure as the stent is deployed. Using a stent oversized relative to the composite graft material results in a smooth, unwrinkled interior surface.

To create a constraining ePTFE material for use in the composite film, the ePTFE is sintered to about 80 to about 100% crystallinity after it has been expanded. To create anisotropically constrained ePTFE, it is expanded and sintered in a single direction which will be the constraining element; while to create isotropically constrained ePTFE, it is expanded in multiple directions and sintered. During stretching in each of the processes, the material tears which leads to the island and node structure that gives ePTFE its porous quality. To create the constraining ePTFE, the PTFE is processed such that the fibril density of the material is greater than the node island density. By way of example, an isotropically constrained ePTFE may be suitable in devices and applications (e.g., inflatable balloons) where a non-compliant material might be desirable.

In contrast, to create ePTFE with greater expansibility characteristics, a lower degree of sintering can be used, typically less than 80%. This leads to an uncoalesced material with lower mechanical strength and inherent structural integrity.

ePTFE as manufactured is a porous material with nodes and fibrils, the size and density of which can be independently controlled during processing. Depending on the use and the desired effect, as for example when rapid and aggressive tissue in-growth (in the case of a graft for use in treating AAA), the ePTFE is processed to have an internodal distance (porosity) ranging from about 35 to about 200 micrometer (μm). To balance optimal tissue compatibility and in-growth with mechanical strength, the internodal distance ranges from about 15 to about 35 μm. An ePTFE material with internodal distance ranging from about 0.1 to about 15 μm may be used for clinically non-porous material to stimulate an encapsulating fibrotic healing response, as opposed to physical in-growth into the material.

Similarly, the selection of the material for the polymeric backbone will have an impact on the composite film. To create a constraining composite film, the polymeric backbone is selected to have high tensile modulus (>1 GPa) and/or a low elongation characteristic (from about 20 to about 150%). In contrast, to create an expansible composite film, the polymeric backbone is selected to have low tensile modulus (<100 MPa) and/or a high elongation characteristic (from about 150 to about 600%).

Suitable thermoplastic materials include polyolefins (e.g. polyethylene, polyester terapthalate, and ethylene vinyl acetates); polyurethanes formulations such as biodurable aromatic polyether (e.g. Biospan, Elasthane); polycarbonates (e.g. Bionate, Chronoflex, Carbothane); silicone modified (e.g. PurSil) polyurethanes; and fluoropolymers (e.g. FEP, PFA, ETFE). The thermoplastic material for use as the polymer backbone will preferentially be sealable using conventional heat sealing technology at temperatures less than about 300° C.

In one exemplary embodiment, the PTFE is stretched in at least one, preferably multiple directions, prior to sintering. The stretching in multiple directions or axes, results in a composite film having reduced expansion or creeping upon inflation.

Burst Tolerance

It is desirable, in particular, in medical applications such as grafts for treating AAA, that the burst tolerance of the composite film be relatively high. In one exemplary embodiment, the structure formed from the composite film has a burst tolerance such that it can be expanded up to 150% of its original unexpanded volume. Such characteristic may be affected by the modulus of elasticity of the selected polymer backbone.

Manufacturability and Construction of Geometric, Inflatable Forms

The composite films, according to the present invention, are highly advantageous for use in forming structures. Factors, including but not limited to the following, affect the manufacturability and the construction of the structures made from the composite films of the present invention: choice of polymer backbone; choice of formation of the composite film (e.g., thermal lamination or spray); method of sealing of the composite film at desirable locations to form the structure; thermal formability; and the presence and incorporation of other elements to either or both the ePTFE and the polymer backbone.

During the making of the composite film, the polymer backbone and the ePTFE may form distinct layers or a composite film having an interface between the ePTFE and the polymer backbone wherein at least some of the polymer backbone penetrates into at least some of the pores of the ePTFE (i.e., it does not fully impregnate the entire thickness of the ePTFE layer). In either scenario, the multi-layered material (i.e., composite film) on the two opposing sides has distinctly two layers, ePTFE and the polymer backbone. The ePTFE and the polymer backbone may be brought together to form the composite film in any number of suitable manners.

One such manner is lamination using a combination of heat and pressure. In an exemplary embodiment, the polymer backbone is formed from a thermoplastic polymer such as, but not limited to: polyolefins, polyurethanes, and/or fluoropolymers.

Heating the thermoplastic polymer to its melting temperature and applying it onto the ePTFE under pressure allows the thermoplastic melt to flow into the pores of the ePTFE material (see FIG. 1B), resulting in a mechanical bond between the two materials. In some instances, due to the chemical similarities between the ePTFE and the fluoropolymer used as the polymer backbone, such as FEP, a thermal lamination between the two materials may further create an additional chemical bond besides the mechanical interlocking.

Typically, the polymer backbone layer has a thickness ranging from about 0.2 to about 3 mils (from about 0.0002 inch to about 0.003 inch). The polymer backbone is thermally laminated onto the surface of the ePTFE at generally about or less than 350° C. As can be appreciated, different polymers used as the polymer backbone may require different lamination temperatures. For example, polyurethanes, polyolefins, and fluoropolymers, may be laminated onto the ePTFE, at temperatures; respectively; from about 100 to about 200° C., from about 100 to about 350° C., and from about 250 to about 350° C. The pressure applied during the lamination process is generally less than about 150 psi.

The thermoplastic materials (e.g., for use as the polymer backbone) can be applied to the ePTFE for thermal lamination in the form of a sheet, or through application of powder dispersions that can be applied to the surface of the ePTFE. After application of heat and pressure, the powder will melt and reflow into a solid, contiguous layer (or a non-contiguous layer, as may be desired and explained further below).

Another suitable method for forming the composite film is "film casting." Using this process, a dispersion/solution comprising the polymer backbone (e.g., silicones, polyurethane) is sprayed onto the surface of the ePTFE (the carrier material) which may be in the form of a flat sheet, a tubing, or any other suitable structure.

Solutions or dispersions of such materials can also be sprayed on or directly applied to the ePTFE material in order to create the composite film. The polymer in solution flows into the pores of the ePTFE through any one or more mechanisms such as wicking, pressure, or any combinations thereof, to create a mechanical interlock between the two materials similar to that shown in FIGS. 1A and 1B. Polymer dispersions typically comprise a percent solid in range from about 0.2 to about 25%. Typically, such dispersions may have a viscosity ranging from about 0.5 cP to about 5000 cP.

The layers of the composite film may be contiguously adjacent one another (e.g., along the entire or substantially the entire length of the interface between the two layers). Alternatively, the composite film may have non-contiguous regions wherein the two layers are not adhered to one another. By way of example, a mask may be placed on some portions of either or both of the layers such that the two layers do not adhere to one another after the composite film has been created. Structures formed from such non-contiguously joined layers may be useful when it is desirable to have agents, such as therapeutic agents contained within such structures to be released to the outside environment of the structure (e.g., within the body of a patient).

Different composite films may be sealed together along one or more portions thereof (as for example, when it is desirable to form a structure using the composite films of the present invention). By way of example, it may be desirable that a seal is formed between the polymer backbone surface of two composite films, or to form a seal between the polymer backbone surface of one composite film and the ePTFE surface of another (or any other variations). Different parameters may be used in selection of the sealing parameters, such as but not limited to, polymer backbone melting temperature, flexural modulus, and percentage elongation. The characteristics of the ePTFE such as but not limited to, pore size/density (e.g., internodal distances ranging from about 0.2 um to about 300 um) and surface activation of the ePTFE for adhesion. By way of example, and as further described below, the surface activation of the ePTFE may be increased by one or more methods.

The conditions of the sealing will further affect the sealing quality and degree between the composite films. Generally, the seal between layers of different composite films is achieved at a temperature ranging from about 100 to about 600° C., normally ranging from about 100° C. to about 250° C. when using thermoplastic material. In an exemplary embodiment, when the composite films simultaneously undergo sealing and cutting, the sealing temperate normally ranges from about 150° C. to about 500° C. Normally, the sealing of the layers of the different composite films is performed under pressures ranging from 0.1 to about 60 psi. By way of example, when the polymer backbone material has a thickness of less than about 1 mil, the pressure ranges from about 5 to about 20 psi; while for polymer backbone material having a thickness ranging from about 1 to about 2 mil, the pressure can range from about 15 to about 60 psi.

Another factor that may be taken under consideration in manufacturing of the composite film is the thermal formability of the material. In an exemplary embodiment, it is advantageous to either or both, to create textured surfaces to enhance sealing and create high aspect ratio preforms through vacuum forming/thermoforming of the polymer backbone of the composite material. Thermoforming (particularly by vacuum forming) is particularly helpful when it is desirable to turn flat sheets or films into parts which have some degree of contours or cavities (such that the film no longer lays flat— see FIGS. 6 and 7). In the case of ePTFE because of both its porous nature and the high temperatures required to process it, thermoforming cannot necessarily be used. However, in a non-porous composite film, the polymer forming the backbone can be manipulated using these processes. The ePTFE is not affected by the temperatures required to thermoform the polymer backbone, but because the ePTFE is mated together with the backbone, it will take the same shape as the final shape of the polymer.

Yet another factor is consideration of introduction of other materials into the ePTFE surface. The introduction may be achieved by thermal lamination of the material between the primary ePTFE and polymer backbone layer. Such materials include, but are not limited to, metallic or polymeric materials. Additionally, or alternatively, polymeric netting or mesh may be selectively added to the composite in order to provide localized or general reinforcement (e.g., tear propagation resistance, expansibility constraint) of the material. Metallic supports in the form of rings, stents, or columns may also be incorporated for structural support to the material. Objects which are anchored by lamination between the layers but have features which penetrate one or both layers (e.g., hooks, barbs) may also be used to aid anchoring or fixation of the composite to other materials.

Surface Modifications

In some exemplary embodiments, another attribute that affects composite films according to the present invention is the surface characteristics of the film.

ePTFE surfaces can be modified by RF induced plasma (using gases such as sulfur dioxide, argon, ammonia, oxygen, etc.), laser roughening, or wet chemical treatment (e.g., sodium/ammonia solution (e.g., Tetratech)) to improve the surface energy of the material. The surface modification can improve the ability of the ePTFE to bond to other materials, such as the polymer backbone or other biologically functional chemicals that would be desirable to add to the exterior of the ePTFE layer. Examples of biologically functional surface modifications that can be applied to ePTFE include the application of fibrin, RGD, or other fibrin precursors to promote thrombogenesis and healing.

The porous nature of ePTFE allows for the use of the composite film (e.g., having a volumetric shape or containment members) as a therapeutic agent delivery device. Therapeutic drugs can be loaded either within the porous matrix alone, or within the containment device formed from the composite material for continuous release after implantation. To enhance the ability of the containment device to serve as a drug reservoir, the composite material may be manufactured to allow selective transfer of the therapeutic agent to the exterior of the device. Another option would be to use a polymer backbone that is porous to allow for transfer of chemicals or materials across the containment membrane (e.g., the agent would transfer from the porous polymer backbone material through the porous ePTFE).

Another such attribute, is the affinity of the polymer backbone to attach (stick to itself—otherwise, tackiness), as for example, when it is folded upon itself or when layers of the same polymer backbone are disposed across from one another. The reduction of the tackiness of the polymer backbone may be advantageous in many circumstances, such as release and expansion of the material from a compact delivery profile to a larger profile. Biocompatible powders such as alumina or tantalum can be used to reduce the surface tackiness of the polymer backbone materials such as silicone and polyurethanes. Chemical groups such as polyethylene glycol (PEG) can be bound to the surface of the polymer backbone material in order to create a hydrophilic surface. Issues with surface tack can also be addressed by selectively laminating a porous mesh comprised of a low surface energy material (e.g., polyester mesh, ePTFE film) to the internal surface of the composite film. The use of ePTFE can also act as a hydrophobic film over the polymer backbone material.

The composite material of a containment device may also be modified by adding sensors (e.g., pressure transducers, strain gauges, temperature sensors, chemical sensors, etc.) to the surface of the material. These sensors can be attached to the material by chemically compatible adhesives or by laminating the sensor directly onto the composite (depending on the function of the sensor) and can be used to monitor in situ conditions within the structures, containment bags, formed from the composite films, and/or its external environment. Using micro-electromechanical device technology, these sensors may be passively powered and/or transdermally (wirelessly) monitored using inductive power and data transfer. The antennae/inductive power coils required for such a function can also be attached directly to the containment unit through the use of chemical adhesives or lamination.

In yet another exemplary embodiment, thrombogenic "flocking" materials such as non-woven polyester/Dacron fibers can be selectively laminated or attached to the polymer backbone of the composite as another method of macro-surface functionalization. Fibers positioned such that they face the interior of the containment bag can also be used to help promote adhesion between the bag and the filling contents.

In some exemplary embodiments, supporting elements can be incorporated into the device structure by lamination or adhesive sealing the supporting elements into the composite film. The supporting elements may range from rigid metallic structures (e.g., mesh, braid, laser-cut or self-expanding stent) to flexible polymeric forms (e.g., mesh, film) and can be used to reinforce the shape the containment device formed from the composite films of the present invention, or to impart physical properties such as increasing the puncture and tear resistance, reducing elongation, improving longitudinal stiffness, etc. Structural elements such as hooks, tethers and barbs may also be attached to the device in order to aid the delivery, placement, and fixation of the device by laminating the elements between the composite layers.

In some exemplary embodiments, supporting structures such as stents, can be incorporated into the ePTFE layer through high temperature sintering prior to application of the polymer backbone. Support structures can range from shape memory materials such as nickel titanium alloys (nitinol) to materials such as stainless steel and cobalt/chromium alloys. After application of the polymer backbone, the supporting structure can be incorporated into a device comprised of a similar ePTFE composite material. The support structure may also be incorporated into a device structure comprised of an ePTFE composite material without additional application of the polymer backbone by allowing the polymer backbone of the remaining structure to be sealed to the ePTFE material of the device using suitable sealing methods.

In certain circumstances, it is useful to ascertain the location of the composite film, in particular, when structures formed from the composite film are used within a patient's body. The diagnostic visualization of the composite film and structures formed therefrom may be achieved by several methods. By way of example, diagnostic visualization may be achieved by addition of materials, visible to the particular diagnostic method, in powder form, as for example premixing of the powder within the polymer backbone, lamination of powder between the ePTFE and the polymer backbone, or preferably, addition of the power to the surface of either or both the ePTFE and the polymer backbone. Other exemplary methods for providing diagnostic visualization is lamination of a bulk material (e.g., trips, beads, rings) between the ePTFE and the polymer backbone; surface texturing of either or both the ePTFE and the polymer backbone, and chemical marking such as the use of fluoroscopic dyes.

Exemplary materials for enhancing diagnostic visualization by means such as CT or MRI, include materials such as ceramic powders (e.g., alumina, tantalum, gadolinium oxide), metallic powders (e.g., Tantalum, platinum alloys), contrast salts (e.g., barium sulfate), and bulk metals (e.g., trips, beads, rings); to either or both the ePTFE and the polymer backbone, preferably the surface of the polymer backbone, or inbetween.

Imparting ultrasonic diagnostic visibility is another feature of some exemplary embodiments (i.e., creating echolucent materials such that they are visible under ultrasound to create a contrast in the echo response of an ultrasound beam between the desired location and the surrounding environment). The contrast within soft tissue can be made by relatively sharp changes in density (e.g., hard/high density materials) and/or echo scattering by changes in surface textures (i.e., recognition can be enhanced using repeating patterns of a diagnostically visible signal caused by the materials and surface of the composite film).

To achieve ultrasound visibility, powders having high hardness such as, but not limited to, ceramic powders including alumina, glass, zirconia; and metallic powders such as titanium; may be added to the surface of the composite film. Alternatively or additionally, stippled/textured formation of surface of the composite film in combination with the hard ceramic or metallic powders may further be useful in imparting ultrasound visibility. By way of example, textured forms can be made by thermoforming the shape of the composite material, or by embedding material within the composite film in a pre-recognizable pattern. In some exemplary embodiments, such material may be added to the polymer backbone or in between the polymer backbone and the ePTFE, using methods similar to those described above.

Imparting fluoroscopic diagnostic visibility is another feature of some exemplary embodiments of the composite films according to the present invention, and structures made thereof. To achieve fluoroscopic visibility, different methods and means may be used, such as addition of highly radiodense powders (e.g., tantalum, tungsten, Pt/Ir compounds), contrast salts (e.g., barium sulfate), bulk metals (e.g., strips, beads, rings; gold, Pt/Ir compounds). Such material may be added to the polymer backbone or in between the polymer backbone and the ePTFE, using methods similar to those described above.

Other Exemplary Embodiments of Containment Devices Made Using Composite Films

As described above, the composite films of the present invention, may be used in a number of ways, to make different structures, and for use in a variety of application. One such structure is a containment member which is usable with medical devices for treatment of a patient, such as treatment of AAA.

In an exemplary embodiment, a containment device is made from a composite ePTFE material with an overall thickness less than about 0.00610" and comprises a layer of ePTFE having a thickness less than about 0.0045" with an IND between ranging from about 0.1 to about 30 microns. The containment member further comprises at least one layer of non-porous thermoplastic polymer backbone material having a total thickness of about less than 0.0025". Suitable thermoplastic materials include polyolefins (e.g. polyethylene, polyester terapthalate, and ethylene vinyl acetates), polyurethanes formulations such as biodurable aromatic polyether (e.g. Biospan, Elasthane), polycarbonate (e.g. Bionate, Chronoflex, Carbothane), silicone modified (e.g. PurSil) polyurethanes, and fluoropolymers (e.g. FEP, PFA, ETFE) that can be sealed using conventional heat sealing technology at temperatures of about less than 300° C. The interior surface of the containment device can be treated with a biocompatible material to increase visualization of the device under CT, as well as specific radiopaque markers (e.g. platinum iridium, gold) to delineate the proximal and distal ends of the device, as well as its rotational orientation. The interior surface may also be treated with an additional layer of material to reduce or eliminate any sticking between the interior surfaces. The greatest diameter of the containment device may range from about 15 to about 120 mm.

The containment device will include a single through lumen and provide filling access. The device will be lined with the composite film such that the ePTFE is oriented along the outward facing surface of the entire device (including the lumen). The lumen of the device will be tapered from a larger proximal diameter (ranging from about 15 to about 70 mm) to a smaller distal diameter (ranging from about 8 to about 34 mm). Proximal and distal cuffs ranging in length from about 0 to about 36 mm and reinforced by internal supports can be incorporated into the device to provide a smooth transition of flow into the lumen of the device. A self expanding stent laminated to the interior lumen of the containment device may also be used to provide additional support.

Although the above description provides a complete and accurate representation of the invention, the present invention may be manifested in a variety of forms other than the specific embodiments described and contemplated herein. Accordingly, departures in form and detail may be made without departing from the scope and spirit of the present invention as described in the appended claims.

What is claimed is:

1. A device for treating an aneurysm, said device comprising:
   a fillable containment bag having two opposing sheets sealed together, each sheet comprising at least one first layer and at least one second layer, the first layer formed from a first material comprising a fluorinated material, and the second layer formed from a second material comprising a polymeric material, wherein the first and second layers are disposed adjacent one another, wherein the first layer comprises a porous fluorinated material and wherein the inflatable containment bag further comprises a single through lumen and filling access, and the containment bag is adapted to conform to the aneurysm.

2. The device according to claim 1, wherein the first layer is oriented along the outward facing surface of the containment bag.

3. The device according to claim 2, wherein the outward facing surface of the containment bag includes the through lumen.

4. The device according to claim 1, wherein the porous first layer has an internodal distances ranging from about 0.2 to about 300 micrometers.

5. The device according to claim 1, wherein the first layer comprises a porous material having a pore size such that the layer is a suitable substrate for in-growth so as to allow incorporation into a host of the aneurysm.

6. The device according to claim 1, wherein the porous first layer has an internodal distance ranging from about 35 to about 200 micrometers so as to promote rapid and aggressive tissue in-growth.

7. The device according to claim 1, wherein the porous first layer is impregnated with the second layer.

8. The device according to claim 7, wherein the impregnation of the first layer with the second layer ranges from about 0.1 to about 95%.

9. The device according to claim 7, wherein the impregnation of the first layer with the second layer ranges from about 5 to about 70%.

10. The device according to claim 7, wherein the first layer is mechanically interlocked with the second layer, the mechanical interlock comprised of the polymer disposed in the pores of the first layer.

11. The device according to claim 1, further comprising a therapeutic drug, wherein the therapeutic drug is disposed within the pores of the first layer.

12. The device according to claim 1, further comprising a therapeutic drug, and wherein the porosity of the first layer is sufficient to permit the flow of the therapeutic drug through the first layer from within the containment bag.

13. The device according to claim 1, further comprising a therapeutic drug, and wherein the porosity of the first layer is sufficient to permit the flow of the therapeutic drug from the second layer of the containment bag.

14. The device according to claim 1, wherein the pores are adapted so as to allow for selective transfer of a therapeutic agent from within the containment bag to the exterior of the containment bag.

15. The device according to claim 1, wherein the first layer and the polymeric second layer comprise different porosities.

16. The device according to claim 15, wherein the porosity of the first and second layer is sufficient to permit transfer of chemicals or materials through the first and second layer.

17. The device according to claim 1, wherein the polymeric second layer comprises a hydrophilic surface.

18. The device according to claim 1, wherein the polymeric layer is bound with polyethylene glycol so as to comprise a hydrophilic surface.

19. The device according to claim 1, wherein the polymer layer comprises a hydrophobic film.

20. The device according to claim 19, wherein the hydrophobic film comprises ePTFE or polyurethane.

21. The device according to claim 1, wherein the containment bag comprises echolucent materials to impart ultrasonic diagnostic visibility thereof.

22. The device according to claim 1, wherein the containment bag comprises radiopaque materials so as to impart fluoroscopic diagnostic visibility to the containment bag.

23. The device according to claim 1, wherein the first layer is manufactured to allow for expansion from a collapsed configuration to an expanded configuration wherein it fills the aneurysm.

24. The device according to claim 1, wherein the first and second layers have a burst tolerance such that the containment bag comprising the first and second layers can be expanded up to 150% of its original unexpanded volume.

25. The device according to claim 1, wherein the first and second layers can expand without failure as a stent is deployed therein.

26. The device according to claim 1, wherein the containment bag comprises longitudinal seams, and wherein the longitudinal seams are oriented parallel to a preferential stretch direction of the first layer so as to withstand a circumferentially exerted tensile load wherein the containment bag fills the aneurysm.

27. The device according to claim 1, wherein the first and second layers have compatible elongation properties to allow the bag to expand without separation of the layers.

28. The device according to claim 27, wherein the polymeric second layer has a high elongation characteristic from about 150% to about 600%.

* * * * *